United States Patent
Kang et al.

(10) Patent No.: US 7,196,177 B2
(45) Date of Patent: Mar. 27, 2007

(54) ANTIBODY VARIABLE REGION OF A MONOCLONAL ANTIBODY AGAINST HUMAN TUMOR NECROSIS FACTOR ALPHA AND A GENE ENCODING THE SAME

(75) Inventors: Heui Il Kang, Seoul (KR); In Young Ko, Anyang-si (KR); Moo Young Song, Suwon-si (KR); Chang Seok Kim, Suwon-si (KR); Sang Koo Park, Suwon-si (KR); Jae Sun Lee, Suwon-si (KR); Tae Hyoung Yoo, Seoul (KR); Kang In Na, Suwon-si (KR)

(73) Assignee: Yuhan Corporation (KR)

( * ) Notice: Subject to any disclaimer, the term of this patent is extended or adjusted under 35 U.S.C. 154(b) by 0 days.

(21) Appl. No.: 11/376,338

(22) Filed: Mar. 16, 2006

(65) Prior Publication Data

US 2006/0147452 A1 Jul. 6, 2006

Related U.S. Application Data

(62) Division of application No. 10/988,617, filed on Nov. 16, 2004.

(30) Foreign Application Priority Data

Nov. 17, 2003 (KR) .................. 10-2003-0080950

(51) Int. Cl.
*C07K 16/00* (2006.01)
*C12P 21/08* (2006.01)

(52) U.S. Cl. ............... 530/388.23; 530/387.1; 530/387.3; 530/388.1

(58) Field of Classification Search ............. None
See application file for complete search history.

(56) References Cited

OTHER PUBLICATIONS

Li et al. Biochemistry 2000. 39:6296-6309.*
C. Chothia et al., "Conformations of immunoglobulin hypervariable regions", *Nature*, vol. 342, Dec. 21-28, 1989, pp. 877-883.
E. Döring et al., "Identification and Characterization of a TNFα Antagonist Derived from a Monoclonal Antibody", *Molecular Immunology*, vol. 31, No. 14, 1994, pp. 1059-1067.
Janeway et al., Immunobiology, p. 3.2, Garland Publishing, New York, 1997.
Rudikoff et al., Proc. Natl. Acad. Sci. 79: 1979-1983 (1982).

* cited by examiner

*Primary Examiner*—Phillip Gambel
*Assistant Examiner*—Chun Crowder
(74) *Attorney, Agent, or Firm*—Sughrue Mion, PLLC

(57) ABSTRACT

An antibody variable region of a monoclonal antibody specifically binding to human tumor necrosis factor-α contains at least one of a heavy chain variable region and a light chain variable region having specific complementarity determining regions therein. A nucleic acid molecule encoding the same, a recombinant vector containing the nucleic acid molecule, and a cell transformed with the recombinant vector are also provided.

5 Claims, No Drawings

SEQUENCE LISTING

```
<160> NUMBER OF SEQ ID NOS: 14

<210> SEQ ID NO 1
<211> LENGTH: 39
<212> TYPE: DNA
<213> ORGANISM: Artificial Sequence
<220> FEATURE:
<223> OTHER INFORMATION: forward primer for heavy chain

<400> SEQUENCE: 1
actagtcgac atggcttggg tgtggaactt gccattcct                          39

<210> SEQ ID NO 2
<211> LENGTH: 35
<212> TYPE: DNA
<213> ORGANISM: Artificial Sequence
<220> FEATURE:
<223> OTHER INFORMATION: reverse primer for heavy chain

<400> SEQUENCE: 2
cccaagcttc caggggccag gggatagacg ggtgg                              35
```

```
<210> SEQ ID NO 3
<211> LENGTH: 39
<212> TYPE: DNA
<213> ORGANISM: Artificial Sequence
<220> FEATURE:
<223> OTHER INFORMATION: forward primer for light chain

<400> SEQUENCE: 3
actagtcgac atggatttac aagtgcagat tttcagctt                          39

<210> SEQ ID NO 4
<211> LENGTH: 30
<212> TYPE: DNA
<213> ORGANISM: Artificial Sequence
<220> FEATURE:
<223> OTHER INFORMATION: reverse primer for light chain

<400> SEQUENCE: 4
cccaagctta ctggatggtg ggaagatgga                                    30

<210> SEQ ID NO 5
<211> LENGTH: 351
<212> TYPE: DNA
<213> ORGANISM: Artificial Sequence
<220> FEATURE:
<223> OTHER INFORMATION: nucleotide sequence of cDNA molecule encoding
      heavy chain variable region

<400> SEQUENCE: 5
caggtccagt tggtgcagtc tggacctgag ctgaagaagc ctggagagac agtcaagatc    60
tcctgcaagg cttctggata taccttcaca cactatggaa tgaactgggt gaagcaggct   120
ccaggagagg gtttaaagtg gatgggctgg ataaacacca acactggaga gccaagatat   180
gatgaagagt tcaagggacg gtttgccttc tctttggaaa cctctgccag cactgcctat   240
ttacagatca acaacctcag acgtgaggac acggctacat atttctgtgc aagatatgat   300
tccaggggat ttgactgctg gggccaaggc accactctca cagtctcctc a            351

<210> SEQ ID NO 6
<211> LENGTH: 327
<212> TYPE: DNA
<213> ORGANISM: Artificial Sequence
<220> FEATURE:
<223> OTHER INFORMATION: nucleotide sequence of cDNA molecule encoding
      light chain variable region

<400> SEQUENCE: 6
caaattgttc tcacccagtc tccagcaatc atgtctgcat ctctagggga acgggtcacc    60
atgacctgca ctgccagctc aagtataagt tacaattact tcactggtta tcagcagagg   120
ccaggatcct cccccaaact ctggatttat agctcatcca atctggcttc tggagtccca   180
cctcgcatca gtggcagtgg gtctgggacc tcttactctc tcacaatcag cagcatggag   240
gctgaagatg ctgccactta ttactgccac cagtatgagc gttccccgtg gacgttcggt   300
ggaggcacca agctggaaat caaacgg                                       327

<210> SEQ ID NO 7
<211> LENGTH: 117
<212> TYPE: PRT
<213> ORGANISM: Artificial Sequence
<220> FEATURE:
<223> OTHER INFORMATION: amino acid sequence of cDNA molecule encoding
      heavy chain variable region
```

<400> SEQUENCE: 7

```
Gln Val Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr His Tyr
             20                  25                  30

Gly Met Asn Trp Val Lys Gln Ala Pro Gly Glu Gly Leu Lys Trp Met
         35                  40                  45

Gly Trp Ile Asn Thr Asn Thr Gly Glu Pro Arg Tyr Asp Glu Glu Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Arg Arg Glu Asp Thr Ala Thr Tyr Phe Cys
                 85                  90                  95

Ala Arg Tyr Asp Ser Arg Gly Phe Asp Cys Trp Gly Gln Gly Thr Thr
                100                 105                 110

Leu Thr Val Ser Ser
            115
```

<210> SEQ ID NO 8
<211> LENGTH: 109
<212> TYPE: PRT
<213> ORGANISM: Artificial Sequence
<220> FEATURE:
<223> OTHER INFORMATION: amino acid sequence of cDNA molecule encoding
      light chain variable region

<400> SEQUENCE: 8

```
Gln Ile Val Leu Thr Gln Ser Pro Ala Ile Met Ser Ala Ser Leu Gly
  1               5                  10                  15

Glu Arg Val Thr Met Thr Cys Thr Ala Ser Ser Ser Ile Ser Tyr Asn
             20                  25                  30

Tyr Phe His Trp Tyr Gln Gln Arg Pro Gly Ser Ser Pro Lys Leu Trp
         35                  40                  45

Ile Tyr Ser Ser Ser Asn Leu Ala Ser Gly Val Pro Pro Arg Ile Ser
     50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr Glu Arg Ser Pro
                 85                  90                  95

Trp Thr Phe Gly Gly Gly Thr Lys Leu Glu Ile Lys Arg
                100                 105
```

<210> SEQ ID NO 9
<211> LENGTH: 5
<212> TYPE: PRT
<213> ORGANISM: Artificial Sequence
<220> FEATURE:
<223> OTHER INFORMATION: heavy chain CDR1

<400> SEQUENCE: 9

```
His Tyr Gly Met Asn
  1               5
```

<210> SEQ ID NO 10
<211> LENGTH: 17
<212> TYPE: PRT
<213> ORGANISM: Artificial Sequence
<220> FEATURE:
<223> OTHER INFORMATION: heavy chain CDR2

-continued

```
<400> SEQUENCE: 10

Trp Ile Asn Thr Asn Thr Gly Glu Pro Arg Tyr Asp Glu Glu Phe Lys
 1               5                  10                  15

Gly

<210> SEQ ID NO 11
<211> LENGTH: 8
<212> TYPE: PRT
<213> ORGANISM: Artificial Sequence
<220> FEATURE:
<223> OTHER INFORMATION: heavy chain CDR3

<400> SEQUENCE: 11

Tyr Asp Ser Arg Gly Phe Asp Cys
 1               5

<210> SEQ ID NO 12
<211> LENGTH: 12
<212> TYPE: PRT
<213> ORGANISM: Artificial Sequence
<220> FEATURE:
<223> OTHER INFORMATION: light chain CDR1

<400> SEQUENCE: 12

Thr Ala Ser Ser Ser Ile Ser Tyr Asn Tyr Phe His
 1               5                  10

<210> SEQ ID NO 13
<211> LENGTH: 7
<212> TYPE: PRT
<213> ORGANISM: Artificial Sequence
<220> FEATURE:
<223> OTHER INFORMATION: light chain CDR2

<400> SEQUENCE: 13

Ser Ser Ser Asn Leu Ala Ser
 1               5

<210> SEQ ID NO 14
<211> LENGTH: 9
<212> TYPE: PRT
<213> ORGANISM: Artificial Sequence
<220> FEATURE:
<223> OTHER INFORMATION: light chain CDR3

<400> SEQUENCE: 14

His Gln Tyr Glu Arg Ser Pro Trp Thr
 1               5
```

ANTIBODY VARIABLE REGION OF A MONOCLONAL ANTIBODY AGAINST HUMAN TUMOR NECROSIS FACTOR ALPHA AND A GENE ENCODING THE SAME

This is a divisional application of pending U.S. application Ser. No. 10/988,617, filed Nov. 16, 2004. The entire disclosure of the prior application, application Ser. No. 10/988,617 is considered part of the disclosure of the accompanying divisional application and is hereby incorporated by reference.

FIELD OF THE INVENTION

The present invention relates to an antibody variable region of a monoclonal antibody specifically binding to human tumor necrosis factor-α, a gene encoding the same, a recombinant vector containing the gene, and a cell transformed with the recombinant vector.

BACKGROUND OF THE INVENTION

Human tumor necrosis factor-α (hereinafter referred to as "hTNFα") is a homotrimer consisting of three 17 kDa protein subunits (Eck M J et al., *JBC* 267: 2119–2122, 1992; Smith R A et al., *JBC* 262: 6951–6954, 1987). hTNFα is an inflammatory cytokine secreted from monocytes and macrophages and functions as a signal transmitter in several cellular reactions such as necrosis and apoptosis (Beyaert R et al., *FEBS Lett.* 340: 9–16, 1994).

hTNFα causes a pro-inflammatory action leading to tissue destruction, such as breakdown of the cartilage and bone (Saklatvala, *Nature* 322: 547–549, 1986) and increasing the adherence of neutrophils and lymphocytes (Pober et al., *K. Immunol.* 138: 3319, 1987). In addition, it has been known that hTNFα plays an important role in a defense mechanism against infectious disease and tumor (Fiers W, *FEBS Lett.* 285: 199–212, 1991).

hTNFα is involved in inflammatory diseases, autoimmune diseases, bacterial infections, cancers and degenerative diseases. Among these diseases, hTNFα has been regarded as a useful target protein for a specific physiological treatment of rheumatoid arthritis and Crohn's disease.

Meanwhile, it has been also suggested to use a hTNFα inhibitor for the purpose of treating rheumatoid arthritis. It has been reported that hTNFα is overexpressed in the synovial cells isolated from the early-stage rheumatoid joint (Buchan G et al., *Clin. Exp. Immunol.* 73: 449–455, 1988), and cytokines relating to rheumatoid arthritis lesions are decreased when the above synovial cells are treated with an anti-hTNFα monoclonal antibody (Butler D M et al., *Eur. Cytokine Netw.* 6: 225–230, 1995).

Further, it has been found that an anti-hTNFα antibody or a recombinant soluble hTNFα receptor suppresses inflammation and destruction of a joint in a collagen induced mouse arthritis model (Wpiquet P F et al., *Immunology* 77: 510–514, 1992; Wooley P H et al., *J. Immunol.* 151: 6602–6607, 1993; Williams R O et al., *Immunology* 84: 433–439, 1995). Moreover, it has been observed that inflammatory arthritis is induced in a transgenic mouse overexpressing hTNFα (Keffer J et al., *EMBO J.* 10: 4025–4031, 1991).

These results indicate that hTNFα plays an important role as a direct or indirect regulator controlling inflammatory cytokines in rheumatoid arthritis. Accordingly, there has been a need to develop a monoclonal antibody having high selectivity and reactivity against hTNFα for the purpose of treating rheumatoid arthritis.

SUMMARY OF THE INVENTION

Accordingly, it is an object of the present invention to provide an antibody variable region of a monoclonal antibody specifically binding to hTNFα.

It is another object of the present invention to provide a gene encoding an antibody variable region of a monoclonal antibody specifically binding to hTNFα; a recombinant vector comprising the gene; and a cell transformed with the recombinant vector.

In accordance with one aspect of the present invention, there is provided an antibody variable region of a monoclonal antibody specifically binding to hTNFα, comprising at least one of:

a heavy chain variable region comprising the amino acid sequences of SEQ ID NOS: 9, 10 and 11; and a light chain variable region comprising the amino acid sequences of SEQ ID NOS: 12, 13 and 14.

In accordance with another aspect of the present invention, there is provided a nucleic acid molecule encoding a heavy chain variable region of a monoclonal antibody specifically binding to hTNFα, wherein the heavy chain variable region comprises the amino acid sequences of SEQ ID NOS: 9, 10 and 11.

In accordance with still another aspect of the present invention, there is provided a nucleic acid molecule encoding a light chain variable region of a monoclonal antibody specifically binding to hTNFα, wherein the light chain variable region comprises the amino acid sequences of SEQ ID NOS: 12, 13 and 14.

DETAILED DESCRIPTION OF THE INVENTION

The present invention encompasses an antibody variable region of a monoclonal antibody specifically binding to hTNFα and a gene encoding the same.

In order to prepare a monoclonal antibody specifically binding to hTNFα, a mouse was immunized with a recombinant hTNFα (Biosource PHC3011, Belgium). Spleen cells obtained from the immunized mouse were fused with myeloma cells (Sp2/0-Ag14, ATCC CRL1581) to prepare a pool of hybridoma cells. Such hybridoma cells were subjected to subsequent cloning and selection procedures, to provide numerous monoclonal antibodies. Among these monoclonal antibodies, certain monoclonal antibodies specifically binding to hTNFα were selected for further analysis. As a result, a hybridoma cell line TSK11 has been obtained, which produces a monoclonal antibody specifically binding to hTNFα and showing a high binding affinity for hTNFα.

Total RNA was extracted from the hybridoma cell line TSK11 and subjected to reverse transcriptase-polymerase chain reaction (RT-PCR) to synthesize cDNA molecules of a heavy chain and a light chain of the monoclonal antibody. Polymerase chain reaction (PCR) was carried out using such cDNA molecules as templates, thereby obtaining a cDNA molecule of about 470 bp encoding a heavy chain variable region and including the nucleotide sequence of SEQ ID NO: 5; and a cDNA molecule of about 450 bp encoding a light chain variable region and including the nucleotide sequence of SEQ ID NO: 6.

As a result of analyzing complementarity determining regions (CDRs) of such heavy chain and light chain variable regions, it has been found that the heavy chain variable region has three CDRs at the amino acid positions of 31–35 (SEQ ID NO: 9), 50–66 (SEQ ID NO: 10) and 99–106 (SEQ ID NO: 11) in the amino acid sequence of SEQ ID NO: 7. Similarly, it has been observed that the light chain variable region has three CDRs at the amino acid positions of 24–35 (SEQ ID NO: 12), 51–57 (SEQ ID NO: 13), and 90–98 (SEQ ID NO: 14) in the amino acid sequence of SEQ ID NO: 8.

Accordingly, a cDNA molecule according to an embodiment of the present invention encodes a heavy chain variable region of a monoclonal antibody specifically binding to hTNFα, wherein the heavy chain variable region includes the amino acid sequences of SEQ ID NOS: 9, 10 and 11. Preferably, the present invention provides a cDNA molecule encoding a heavy chain variable region containing the amino acid sequence of SEQ ID NO: 7 and, more preferably, a cDNA molecule having the nucleotide sequence of SEQ ID NO: 5.

Further, a cDNA molecule according to another embodiment of the present invention encodes a light chain variable region of a monoclonal antibody specifically binding to hTNFα, wherein the light chain variable region includes the amino acid sequences of SEQ ID NOS: 12, 13 and 14. Preferably, the present invention provides a cDNA molecule encoding a light chain variable region containing the amino acid sequence of SEQ ID NO: 8 and, more preferably, a cDNA molecule having the nucleotide sequence of SEQ ID NO: 6.

Each of the foregoing cDNA molecules encoding the heavy chain variable region and the light chain variable region may be inserted into a conventional vector to obtain a recombinant vector. In a preferred embodiment of the present invention, the cDNA molecule including the nucleotide sequence of SEQ ID NO: 5 or 6 may be inserted into pCR2.1-TOPO (Invitrogen Co. U.S.A.) to prepare a recombinant vector pTSK11-Hv containing the heavy chain variable region or a recombinant vector pTSK11-Lv containing the light chain variable region.

Further, such recombinant vector may be introduced into a suitable host, e.g., a microorganism such as *E. coli* TOP10F. For example, *E. coli* TOP10F was transformed with either pTSK11-Hv or pTSK11-Lv to obtain an *E. coli* transformants designated *E. coli* TOP10F/pTSK11-Hv and *E. coli* TOP10F/pTSK11-Lv, respectively, which were deposited at the Korean Collection for Type Cultures (Address: #52, Oun-dong, Yusong-ku, Taejon 305–333, Republic of Korea) on Aug. 26, 2003 under the accession numbers of KCTC 10514BP and KCTC 10515BP, respectively in accordance with the terms of the Budapest Treaty on the International Recognition of the Deposit of Microorganisms for the Purposes of Patent Procedure.

The above recombinant vector may be recovered from the transformant according to a conventional method (J. Sambrook et al., *Molecular cloning* Vol. 1:1.25–1.28). For example, the transformant may be treated with solution 1 (50 mM glucose, 25 mM Tris·HCl and 10 mM EDTA) to weaken its cell membrane, followed by treating with solution 2 (0.2 N NaOH and 1% SDS) to destroy the cell membrane completely and denature the exposed proteins and chromosomes. Next, cellular components except for the recombinant vector may be aggregated by further treating with solution 3 (5 M potassium acetate and acetic acid) and, then, the resulting solution may be subjected to centrifugation to obtain a supernatant containing the recombinant vector. The recombinant vector may be recovered from the supernatant by way of ethanol precipitation.

An antibody variable region of the present invention may comprise at least one of the heavy chain variable region containing the amino acid sequences of SEQ ID NOS: 9, 10 and 11; and the light chain variable region containing the amino acid sequences of SEQ ID NOS: 12, 13 and 14. Preferably, the antibody variable region may comprise at least one of the heavy chain variable region having the amino acid sequence of SEQ ID NO: 7 and the light chain variable region having the amino acid sequence of SEQ ID NO: 8.

A humanized monoclonal antibody against hTNFα may be obtained by fusing a human antibody gene with a cDNA molecule encoding a heavy chain variable region containing CDRs of SEQ ID NOS: 9 to 11 or encoding a light chain variable region containing CDRs of SEQ ID NOS: 12 to 14. Alternatively, a humanized monoclonal antibody may be obtained by replacing a human antibody variable region with such cDNA molecule.

As mentioned above, since the antibody variable region of the present invention specifically binds to hTNFα, it can be effectively used for neutralizing and deactivating hTNFα.

The present invention is further defined in the following Examples. It should be understood that these Examples, while indicating preferred embodiments of the invention, are given by way of illustration only.

EXAMPLE 1

Immunization of a Mouse with hTNFα

30 µg of a recombinant hTNFα (Biosource PHC3011, Belgium) dissolved in 150 µl of phosphate buffered saline (PBS) was emulsified by mixing with 150 µl of complete Freund's adjuvant (Sigma F5881, U.S.A.), and 300 µl of the resulting emulsion was injected intraperitoneally (i.p.) into a 6-week old male BALB/c mouse. After two weeks, the mouse was injected i.p. with 300 µl of emulsion mixture containing 30 µg of hTNFα and 150 µl of incomplete Freund's adjuvant (Sigma F5506, USA). Two weeks after the second injection, 30 µg of the recombinant hTNF-α dissolved in 150 µl of PBS was injected intravenously (i.v.) into the mouse. 10 days after the third injection, the mouse was boosted i.v. with 30 µg of the recombinant hTNFα in PBS.

EXAMPLE 2

Fusion of Mouse Spleen Cells Producing Anti-hTNFα Antibody

The immunized mouse in Example 1 was sacrificed by potassium carbonate suffocation and, then, the spleen was extracted therefrom. Spleen cells were obtained from the mouse spleen, and mixed with nonsecreting myeloma cells, Sp2/0 (ATCC CRL1581) at a ratio of 10:1. For cell fusion, 1 ml of 50% polyethylene glycol (PEG 1500, Roche 783641) preheated to 37° C. was added to the cell mixture. Fused cells were diluted with a growth medium containing 20% fetal bovine serum (FBS, JRH, 12-10678P), 50 µg/ml of gentamicin (Gibco-BRL, 15750-060), 1×DMEM (JRH, 56499-10L) and 1×HAT supplement (0.1 mM sodium hypoxanthine, 0.4 µM aminopterin, 16 µM thymidin; Gibco-BRL, 31062-037) and distributed in 0.2 ml aliquots to a 96-well plate (Nunc, 469949, Denmark) at a concentration of 1.1×10⁵ cells/well. The fused cells were cultured at 37° C. in a humidified CO$_2$ incubator with 5% CO$_2$ for 2~3 weeks.

EXAMPLE 3

Screening and Cloning of a Cell Line Producing Anti-hTNFα Antibody

Once the fused cells formed colonies, their supernatant was taken and subjected to ELISA assay to confirm antibody production. For ELISA assay, wells were coated with 1 μg/mg of hTNFα at 4° C. overnight, 200 μl of 0.5% casein-PBS solution was added to each well, and the reaction was carried out at 37° C. for 1 hour. Next, 100 μl of the supernatant was added to the each well, and the reaction was carried out at 37° C. for 2 hours. Then, 100 μl of horseradish peroxidase-conjugated goat anti-mouse IgG (Bio-Rad, 170–6516) diluted by a ratio of 1:1000 was added to the each well and kept at 37° C. for 1.5 hours. Lastly, 100 μl of a horseradish peroxiadase substrate solution (Bio-Rad, 172–1064) was added to the each well and such well was maintained at 37° C. for 3 minutes to induce color development. The absorbance of the each well was measured at 410 nm with ELISA reader (Dinatec inc., USA).

EXAMPLE 4

Selection of a Cell Line Producing Anti-hTNFα Antibody

Among the cell lines cloned in Example 3, nine IgG-producing cell lines, which showed higher absorbance than a positive control serum obtained from a hTNF-α immunized mouse, were obtained. Out of these cell lines, TSK11 exhibiting the highest absorbance was finally selected for further analysis.

EXAMPLE 5

Isotyping of Monoclonal Antibody Obtained from Hybridoma Cell Line TSK11

The isotype of the monoclonal antibody produced from the hybridoma cell line TSK11 was determined by ELISA assay as follows. 100 μl of mouse MonoAb ID kit HRP solution (Zymed, 90-6550) was added to a well previously coated with 100 μg/ml of TSK11 antibody and, then, the well plate was kept at room temperature for 3 minutes to induce color development. The absorbance of each well was measured at 410 nm with ELISA reader (Dinatec inc., U.S.A.). As a result, it was found that the TSK11 antibody contains an IgG1-type heavy chain and a kappa-type light chain.

EXAMPLE 6

In vitro Binding Affinity of Monoclonal Antibody from Hybridoma Cell Line TSK11

In vitro binding affinity of TSK11 antibody against hTNFα was determined by ELISA assay. Here, each well was coated with 100 μl of recombinant hTNFα at a concentration of 4 μg/ml. Next, in Micro Tube (AXYGEN, U.S.A.) recombinant hTNFα was diluted with PBS solution supplemented with 0.02% bovine serum albumin to obtain the final concentration ranging from $5\times10^{-9}$ M to $1\times10^{-10}$ M. hTNFα diluents having various concentrations were mixed with 30 ng of TSK11 antibody and maintained at 37° C. for 2 hours. The mixed solution was distributed to the each well coated with the recombinant hTNFα, and incubated at 37° C. for 2 hours. Then, 100 μl of a horseradish peroxiadase substrate solution (Bio-rad, 172-1064) was added to the each well and kept at 37° C. for 3 minutes to induce color development. The absorbance of the each well was measured at 410 nm with ELISA reader (Dinatec inc., U.S.A.).

Apparent affinity was determined by calculating a reciprocal of the antigen concentration required in inhibiting 50% of the maximum binding in the competitive ELISA according to Scatchard plot analysis (Friguet E. et al., *J. of Immunological Method* 77: 305–319, 1985). As a result, the affinity of TSK11 antibody against hTNFα was $1.95\times10^{-9}$ M (Kd).

EXAMPLE 7

RNA Isolation from Hybridoma Cell Line TSK11 and cDNA Synthesis

Total RNA was extracted from 1×10⁸ cells of hybridoma cell line TSK11 with RNeasy kit (QIAGEN, U.S.A.) and subjected to cDNA synthesis using Thermotranscript Kit (GibcoBRL, U.S.A.). 5 μg of RNA as a template and 0.5 ng of Oligo d(T) were suspended in distilled water whose final volume was adjusted to 10 μl. The mixture was kept at 65° C. for 5 minutes to denature RNA and cooled down to room temperature to induce primer annealing. RT-PCR reaction solution for cDNA synthesis was prepared by mixing 1 μl of reverse transcriptase (1 unit/μl), 2.5 μl of 0.1 M DTT, 2.5 μl of 10 mM dNTP and 1 μl of RNase inhibitor (1 unit/μl) whose final volume was adjusted to 25 μl with distilled water. The RT-PCR reaction was performed at 50° C. for 1 hour and stopped by heating the reaction mixture at 95° C. for 5 minutes.

PCR was conducted by employing 2 μg of the synthesized cDNA as a template and a pair of primers (SEQ ID NOS: 1 and 2) for the amplification of a heavy chain or another pair of primers (SEQ ID NOS: 3 and 4) for the amplification of a light chain. The PCR reaction solution contained 0.5 μl of AmpliTaq® Gold polymerase (5 unit/μl, Perkin-Elmer Biosystem Co., U.S.A.), 1 μl of 10 mM dNTP and 5 μl of 25 mM MgCl$_2$ whose final volume was adjusted to 50 μl with distilled water. The PCR conditions were as follows: 30 cycles of 1 minute at 94° C., 1 minute at 55° C. and 2 minutes at 72° C. after an initial denaturation of 5 minutes at 95° C., and followed by a final extension of 10 minutes at 72° C.

The amplified DNA was subjected to 1.5% agarose gel electrophoresis and the gel was stained with 100 ml of 0.5 μg/ml ethidium bromide solution for 20 minutes. As a result, two amplified DNA products were identified at a position corresponding to about 470 bp in case of the heavy chain and at a position corresponding to about 450 bp in case of the light chain, based on a 100 bp standard DNA ladder (Lifetechnology Co. U.S.A.).

EXAMPLE 8 cDNA Cloning

The heavy chain DNA fragment of 470 bp amplified in Example 7 was recovered and purified from the agarose gel by using QIAquick™ Gel Extraction kit (Qiagen, U.S.A.). The purified DNA fragment was subcloned into vector pCR2.1-TOPO (Invitrogen Co., U.S.A.) and the resulting vector was introduced into *E. coli* TOP10F (Invitrogen Co., U.S.A.) to obtain a transformant (Cohen, S. N. et al., *Proc. Nat. Acad Sci.* 69: 2110, 1972). The *E. coli* transformant thus prepared was cultured overnight in LB medium supplemented with 100 µg/Ml of ampicillin. A plasmid DNA was extracted from the cultured transformant and treated with restriction enzyme EcoRI (BioLab Co., USA), to obtain a clone TSK11-Hv containing the heavy chain DNA fragment of 470 bp.

The same procedures were performed as to the light chain DNA fragment of 450 bp amplified in Example 7 to obtain an *E. coli* TOP10F transformant. The *E. coli* transformant was cultured overnight in LB medium supplemented with 100 µg/ml of ampicillin. A plasmid DNA was extracted from the cultured transformant and treated with restriction enzyme EcoRI (BioLab Co., USA), to obtain a clone TSK11-Lv containing the light chain DNA fragment of 450 bp.

EXAMPLE 9 cDNA Nucleotide Sequencing

Clones TSK11-Hv and TSK11-Lv obtained in Example 8 were purified by using Wizard® plus SV Minipreps DNA Purification System (Promega, U.S.A.), and subjected to nucleotide sequencing.

As a result, it was found that the heavy chain DNA fragment contained the nucleotide sequence of SEQ ID NO: 5 and the amino acid sequence of SEQ ID NO: 7. Three specific DNA fragments (TSK11Hv1, TSK11Hv2 and TSK11Hv3) belonging to clone TSK11Hv were tested, and their nucleotide sequences were identical. A plasmid vector obtained from the clone TSK11Hv was designated pTSK11-Hv. Further, *E. coli* transformed with the plasmid vector pTSK11-Hv was designated *E. coli* TOP10F/pTSK11-Hv and deposited at the Korean Collection for Type Cultures (Address: #52, Oun-dong, Yusong-ku, Taejon 305–333, Republic of Korea) on Aug. 26, 2003 under the accession number of KCTC 10514BP, in accordance with the terms of the Budapest Treaty on the International Recognition of the Deposit of Microorganisms for the Purposes of Patent Procedure.

Further, it was observed that the light chain DNA fragment contained the nucleotide sequence of SEQ ID NO: 6 and the amino acid sequence of SEQ ID NO: 8. Two specific DNA fragments (TSK11Lv1 and TSK11Lv2) belonging to clone TSK11Lv were tested, and their nucleotide sequences were identical. A plasmid vector obtained from the clone TSK11Lv was designated pTSK1-Lv. Further, *E. coli* transformed with the plasmid vector pTSK11-Lv was designated *E. coli* TOP10F/pTSK11-Lv and deposited at the Korean Collection for Type Cultures (Address: #52, Oun-dong, Yusong-ku, Taejon 305–333, Republic of Korea) on Aug. 26, 2003 under the accession number of KCTC 10515BP, in accordance with the terms of the Budapest Treaty on the International Recognition of the Deposit of Microorganisms for the Purposes of Patent Procedure.

Based on the amino acid sequence analysis (Harris. L. et al., *Protein Sci.* 4: 306–310, 1995; Kabat. E. A. et al., *Sequence of proteins of immunological interest.* 5th Ed., 1991; Williams A. F. et al., *Annu. Rev. Immunol.* 6: 381–406, 1988) of the variable region of the monoclonal antibody obtained from the hybridoma cell line TSK11, it was found that the heavy chain belongs to a miscellaneous group other than 11 groups defined by Kabat and the light chain belongs to a kappa 6-type subgroup.

Antigen-recognizing CDRs of the heavy chain were found to be at the amino acid positions of 31–35 (SEQ ID NO: 9), 50–66 (SEQ ID NO: 10), and 99–106 (SEQ ID NO: 11) and those of the light chain were found to be at the amino acid positions of 24–35 (SEQ ID NO: 12), 51–57 (SEQ ID NO: 13), and 90–98 (SEQ ID NO: 14).

While the embodiments of the subject invention have been described and illustrated, it is obvious that various changes and modifications can be made therein without departing from the spirit of the present invention which should be limited only by the scope of the appended claims.

What is claimed is:

1. An isolated antibody variable region of a monoclonal antibody specifically binding to human tumor necrosis factor-α, comprising:
a heavy chain variable region comprising the amino acid sequences of SEQ ID NOS: 9, 10 and 11; and
a light chain variable region comprising the amino acid sequences of SEQ ID NOS: 12, 13, and 14.

2. The antibody variable region of claim 1, wherein the heavy chain variable region comprises the amino acid sequence of SEQ ID NO: 7.

3. The antibody variable region of claim 1, wherein the light chain variable region comprises the amino acid sequence of SEQ ID NO: 8.

4. The antibody variable region of claim 1, wherein the heavy chain variable region is encoded by a cDNA molecule comprising the nucleotide sequence of SEQ ID NO: 5.

5. The antibody variable region of claim 1, wherein the light chain variable region is encoded by a cDNA molecule comprising the nucleotide sequence of SEQ ID NO: 6.

* * * * *